United States Patent
Nguyen et al.

[11] Patent Number: 5,827,218
[45] Date of Patent: Oct. 27, 1998

[54] SURGICAL SUCTION POOL TIP

[75] Inventors: John Nguyen, San Jose; Charles Nelson, Pleasanton, both of Calif.

[73] Assignee: Stryker Corporation, Kalamazoo, Mich.

[21] Appl. No.: 634,652

[22] Filed: Apr. 18, 1996

[51] Int. Cl.⁶ ........................................... A61M 1/00
[52] U.S. Cl. ........................... 604/30; 604/34; 604/35; 604/247; 604/902; 137/860
[58] Field of Search .................... 604/27, 34, 35, 604/173, 39, 902, 247, 30, 43, 118; 128/912; 277/29, 134, 152; 137/834, 860

[56] References Cited

U.S. PATENT DOCUMENTS

| | | |
|---|---|---|
| 1,317,851 | 10/1919 | Arnett . |
| 2,243,299 | 5/1941 | Travers . |
| 2,531,793 | 11/1950 | Sulek . |
| 3,469,582 | 9/1969 | Jackson . |
| 3,771,522 | 11/1973 | Waysilk et al. . |
| 3,912,168 | 10/1975 | Mullins et al. . |
| 4,361,187 | 11/1982 | Luers ............... 137/860 |
| 4,400,168 | 8/1983 | Buechel et al. . |
| 4,941,872 | 7/1990 | Felix et al. . |
| 5,186,714 | 2/1993 | Boudreault et al. . |
| 5,188,591 | 2/1993 | Dorsey, III . |
| 5,203,769 | 4/1993 | Clement et al. . |
| 5,224,929 | 7/1993 | Remiszewski . |
| 5,261,905 | 11/1993 | Doresey, III . |
| 5,281,201 | 1/1994 | Dorsey, III . |
| 5,295,956 | 3/1994 | Bales et al. . |
| 5,349,950 | 9/1994 | Ulrich et al. ............... 604/35 |
| 5,350,356 | 9/1994 | Bales et al. ............... 604/27 |
| 5,391,145 | 2/1995 | Dorsey, III . |
| 5,447,494 | 9/1995 | Dorsey, III ............... 604/27 |

FOREIGN PATENT DOCUMENTS

| | | |
|---|---|---|
| WO86/04247 | 7/1986 | WIPO . |
| WO93/17733 | 9/1993 | WIPO . |
| WO94/13335 | 6/1994 | WIPO . |
| WO94/19030 | 9/1994 | WIPO . |
| WO94/23773 | 10/1994 | WIPO . |

OTHER PUBLICATIONS

Installation/Operating Instructions for Nezhat–Dorsey Hydro–Dissection System "Quick–Disconnect" Probe Tips information booklet, American Hydro–Surgical Instruments, Inc. (2 pages).

*Primary Examiner*—Mark Bockelman
*Attorney, Agent, or Firm*—Flynn, Thiel, Boutell & Tanis, P.C.

[57] ABSTRACT

An improved suction tip for a surgical irrigation apparatus which tip includes an outer tube having a distal end portion for communication with a surgical site and a proximal end for communication with a suction irrigation handpiece, and an inner tube extending in the outer tube and having an open distal end portion for communication with the surgical site and an open proximal end portion for communication with the handpiece. A one way seal is interposed between the inner and outer tubes of the tip. The hub defining the proximal end portion of the outer tube has a single internal thread for connection to both the handpiece and inner tube.

15 Claims, 7 Drawing Sheets

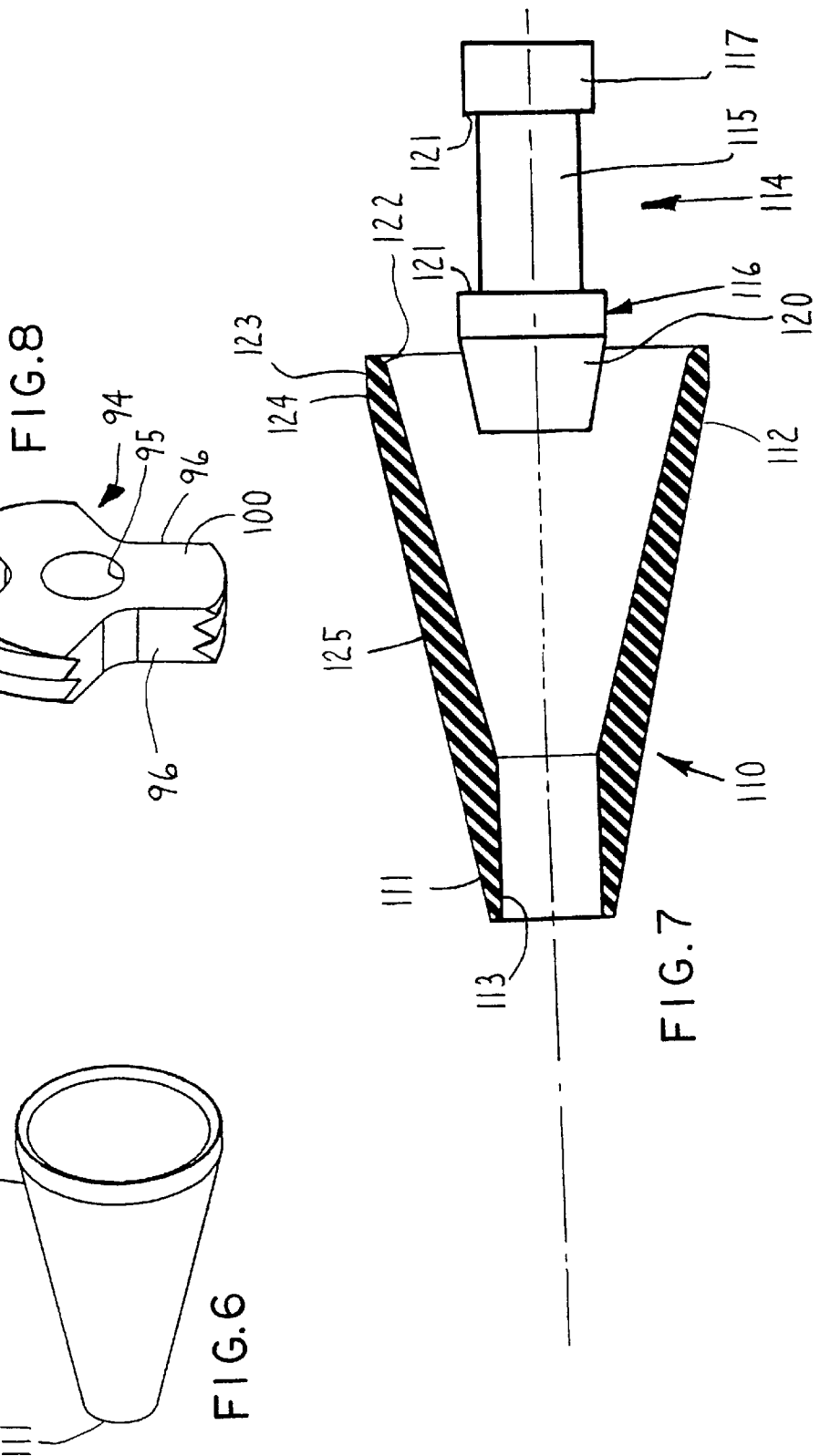

5,827,218

SURGICAL SUCTION POOL TIP

FIELD OF THE INVENTION

This invention relates to a surgical suction pool tip for minimizing turbulence near sensitive organs during suction by a surgical suction irrigation apparatus.

BACKGROUND OF THE INVENTION

Surgical suction pool tips are known wherein an outer tube has a turbulence minimizing distal end portion for insertion in a surgical site and a proximal end portion connectable to a suction irrigation passage of a suction irrigation handpiece. Such known suction pool tips have included an inner tube extending in the outer tube and having an open distal end portion for communication with the surgical site and having an open proximal end for connection to such a suction irrigation passage of a suction irrigation handpiece.

In one device available on the market, a seal is required between the outside of the inner tube and the inside of the handpiece, relatively close tolerances are required as between the inner tube and handpiece, and the design of the handpiece and at least the inner tube of the tip are co-dependent (not independent). Further, entirely different fixation systems are used to interconnect the outer tube to the inner tube and the outer tube to the handpiece. Further, the interconnection of tip and handpiece is not mechanically positive, but rather relies on a resilient connection. Further, to the extent the seal between inner tube and handpiece remains intact, the inner tube can serve only one function, namely irrigation flow to a surgical site, and cannot be used in combination with the outer tube for combined suction flow from the surgical site.

Accordingly, the objects and purposes of the present invention include provision of a suction irrigation tip which avoids the disadvantages of the mentioned marketed tip.

SUMMARY OF THE INVENTION

An improved suction tip for a surgical irrigation apparatus which tip includes an outer tube having a distal end portion for communication with a surgical site and a proximal end for communication with a suction irrigation handpiece, and an inner tube extending in the outer tube and having an open distal end portion for communication with the surgical site and an open proximal end portion for communication with the handpiece. In one embodiment of the invention, a one-way seal is interposed between the inner and outer tubes of the tip. In another embodiment of the invention, the hub defining the proximal end portion of the outer tube has a single internal thread for connection to both the handpiece and inner tube.

Further objects and purposes of the invention will be apparent to persons acquainted with apparatus of this general type upon reading the following description and reviewing the accompanying drawings.

BRIEF DESCRIPTION OF THE DRAWINGS

FIG. 6 is a pictorial view of the cone seal in FIG. 4A.

FIG. 7 is an enlarged, exploded, central cross-sectional view of the cone seal and its tubular adaptor of FIG. 4A.

FIG. 8 is an enlarged pictorial view of the spider collar of FIG. 4A.

DETAILED DESCRIPTION

Figure 1:
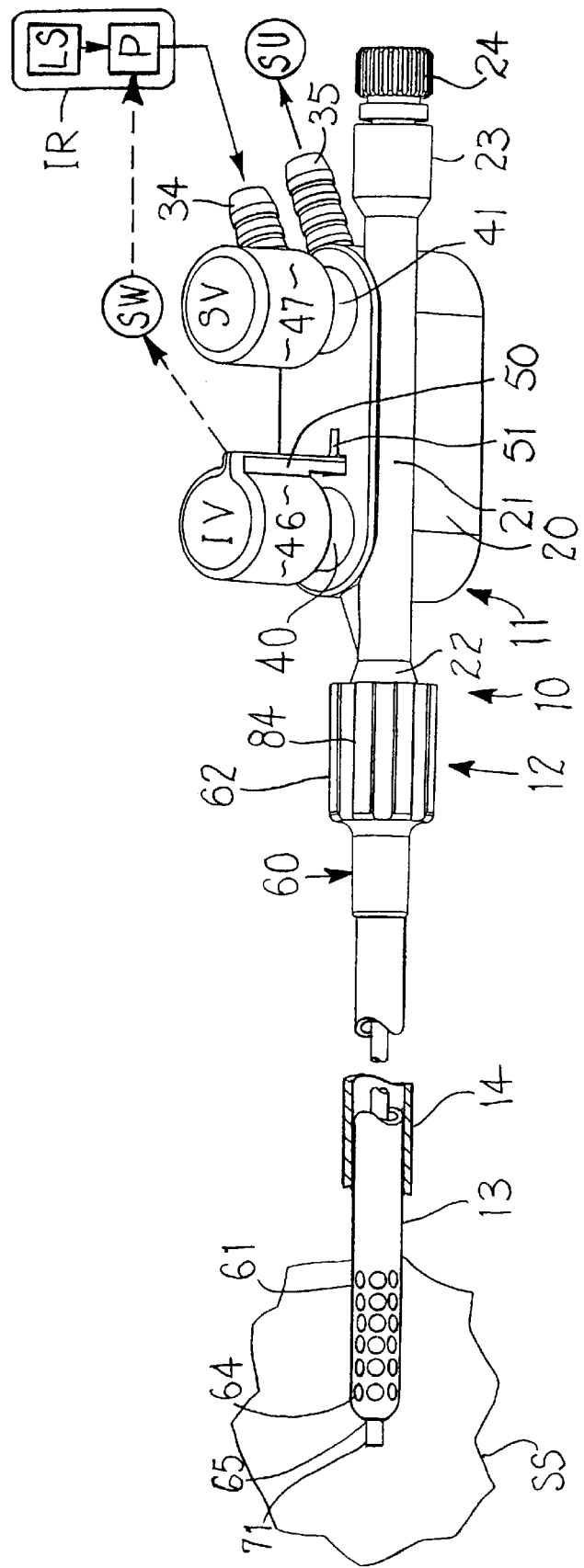
FIG. 1 is a fragmentary pictorial view of an apparatus embodying the invention.

A surgical suction irrigation apparatus 10 (FIG. 1), embodying the invention, comprises a suction irrigation handpiece 11 and a suction irrigation tip 12 extending forward (leftward in FIG. 1) from the handpiece 11 for insertion of its forward end portion 13 into a surgical site SS on a patient for providing suction and irrigation service during surgery. The tip 12 may be inserted into the surgical site SS through an endoscopic cannula of any conventional type, schematically indicated by the fragment 14.

The tip 12 can be used with a variety of suction irrigation handpieces but the handpiece 11 here shown, by way of example, is preferably that disclosed in U.S. application 08/502 708 (Attorney Reference S*E 139A) assigned to the Assignee of the present invention.

Figure 3:
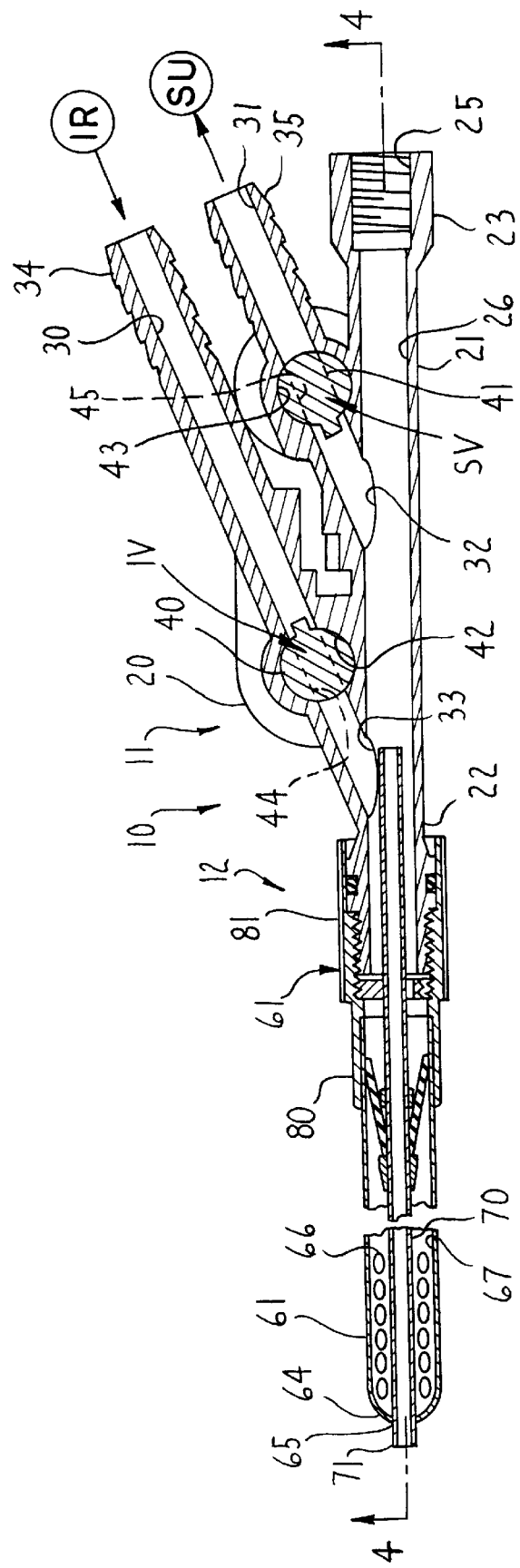
FIG. 3 is a central cross-sectional view of the tip and corresponding part of the handpiece, as seen from above in FIG. 1 and generally corresponding to the cutting line 3—3 of FIG. 4.
Figure 4:
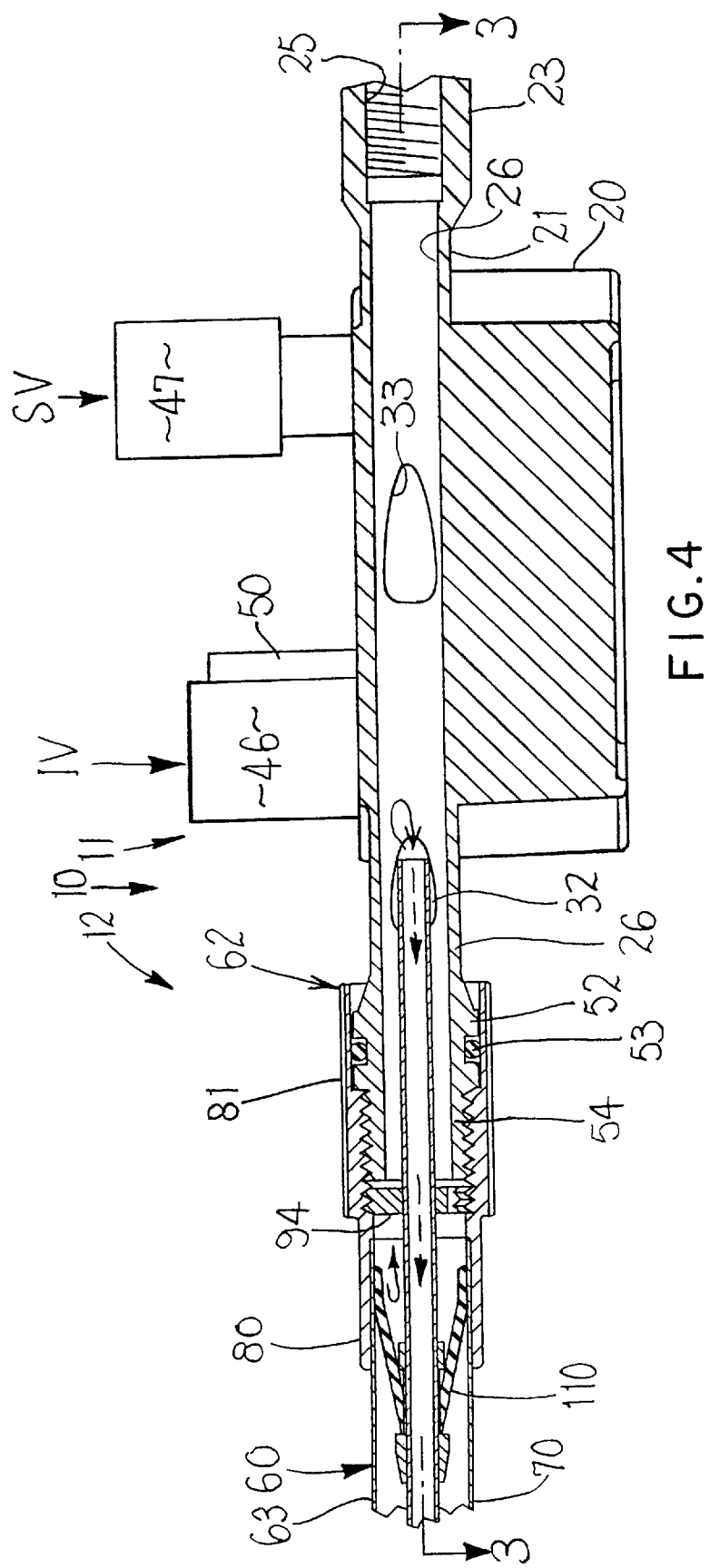
FIG. 4 is a fragmentary enlarged central cross-sectional view taken substantially on the line 4—4 of FIG. 3.

The handpiece 11 comprises a housing 20 preferably of molded plastic and including a suction irrigation conduit 21. The conduit 21 is open from end to end and extends both rearwardly and forwardly beyond the remainder of the housing 20. The forward end portion 22 is adapted to connect, as hereafter discussed, to the rear end of the tip 12 or alternatively to some other desired tip or tool (not shown). The rear end portion 23 of the conduit 21 is adapted to receive a tool (not shown) of any desired type or, as here shown, to be closed by a removable cap 24 for sealingly closing the rear end of the conduit 21. In the embodiment shown, the rear end portion 23 of the conduit 21 is internally threaded as generally indicated at 25 (FIGS. 3 and 4). The conduit 21 has a central passage 26 (FIG. 4) opening longitudinally from end to end therethrough.

The housing 20 includes front and rear fluid passages 30 and 31 respectively (FIG. 3). The passages 26, 30 and 31 are here coplanar. The passages 30 and 31 communicate at their front ends with the passage 26 at respective forward and rearward ports 32 and 33 and angle away therefrom and rearwardly to open through nipples, or other suitable fittings, 34 and 35 respectively projecting rearward from the main body of the handpiece housing 20 for connection to suitable fluid handling means, typically an irrigation liquid source IR and suction source SU of conventional type. Preferably the irrigation liquid source IR is connected to the front passage 30 and the suction source SU is connected to the rear passage 31, at the respective nipples 34 and 35, for supplying irrigation liquid and suction through the respective ports 32 and 33 communicating with the central passage 26 of the conduit 21.

The housing 20 includes a pair of manually actuable valves IV and SV, here of normally closed, push to open type for controlling irrigation liquid flow and suction flow through the passages 30 and 31 respectively (FIGS. 1 and 3). The valves IV and SV include respective valve plungers schematically indicated at 40 and 41 in FIG. 3, independently reciprocable in parallel bores 42 and 43 respectively in the housing 20. The valve bores 42 and 43 extend diametrally across the respective irrigation and suction passages 30 and 31, preferably perpendicular to the plane of the passages 26, 30 and 31, and hence substantially downward in FIG. 1. In their up position shown in FIGS. 1 and 3, the valve plungers 40 and 41 sealingly block the respective irrigation and suction passages 30 and 31. However, the plungers 40 and 41 are each provided with means to open their respective passages 30 and 31 upon downward displacement of their respective plungers 40 and 41 from their up FIG. 1 and FIG. 3 position, such flow opening means here being schematically represented in broken line by diametral through holes 44 and 45, respectively. Downward displacement of the corresponding valve plunger 40 or 41 will align the corresponding diametral through hole 44 or 45 with the corresponding passage 30 or 31 to open such passage, and thus connect the corresponding nipple 34 or 35 with the passage 26. The plungers 40 and 41 are preferably spring biased upward by suitable coaxially aligned compression springs (not shown) in the bottoms of the valve bores 42 and 43 respectively, to close the passages 30 and 31 as aforementioned. The valve plungers 40 and 41 are provided with suitable seal means (not shown) coacting with the valve bores 42 and 43 respectively to prevent fluid leakage along the respective passages 30 and 31 with the plungers 40 and 41 in their passage closing up positions shown in FIGS. 1 and 3. The above mentioned springs and seal means (not shown) may be of any conventional type.

The upper ends of the valve plungers 40 and 41 have radially enlarged heads 46 and 47 respectively (FIG. 1), engageable by a finger or thumb of the user for depressing the corresponding valve plunger. The radially enlarged heads 46 and 47 limit the downward displacement of the corresponding valve plungers to accurately locate the diametral through holes 44 and 45 (FIG. 3) substantially coaxially, and in fluid flow relation, with the corresponding irrigation and suction passages 30 and 31, i.e. to establish the open, plunger down (in reference to the orientation of the apparatus in FIG. 1) position of the respective valve plunger.

In the FIG. 1 example depression of the irrigation valve plunger 40 to open the irrigation passage 30, also actuates a switch SW to actuate an irrigation liquid pump P fed by a conventional irrigation liquid supply LS, the irrigation liquid source IR in that instance comprising the liquid supply and pump P connected to the irrigation liquid nipple 34, all as schematically indicated in FIG. 1. In the example shown, the switch SW is located within the housing 20, by any convenient means not shown, and is actuated by downward displacement of the bottom of a rib 50 fixed on the side of the valve plunger head 46 and extending down through a hole 51 in the top of the housing 20. However, for purposes of the present invention, the switch SW can be otherwise actuated and located, or the switch and pump can be eliminated in favor of a gravity irrigation liquid feed to the nipple 34 or by some other suitable pressure feed of irrigation liquid to the nipple 34.

The front end portion 22 (FIG. 4) of the conduit 21 comprises a radially enlarged boss 52 carrying an annular seal, preferably a conventional 0-ring 53 in a radially outwardly opening annular groove on the boss 52. The front end portion of the conduit 21 further includes an externally threaded sleeve-like part 54 extending coaxially forward from the boss 52.

To the extent above described, the handpiece 11 is preferably similar to that disclosed in above mentioned pending U.S. application Ser. No. 08/502 708 (Attorney's Reference S*E 139A), assigned to the assignee of the present invention. However, a desired other handpiece construction may be substituted, within the scope of the present invention.

Figure 2:
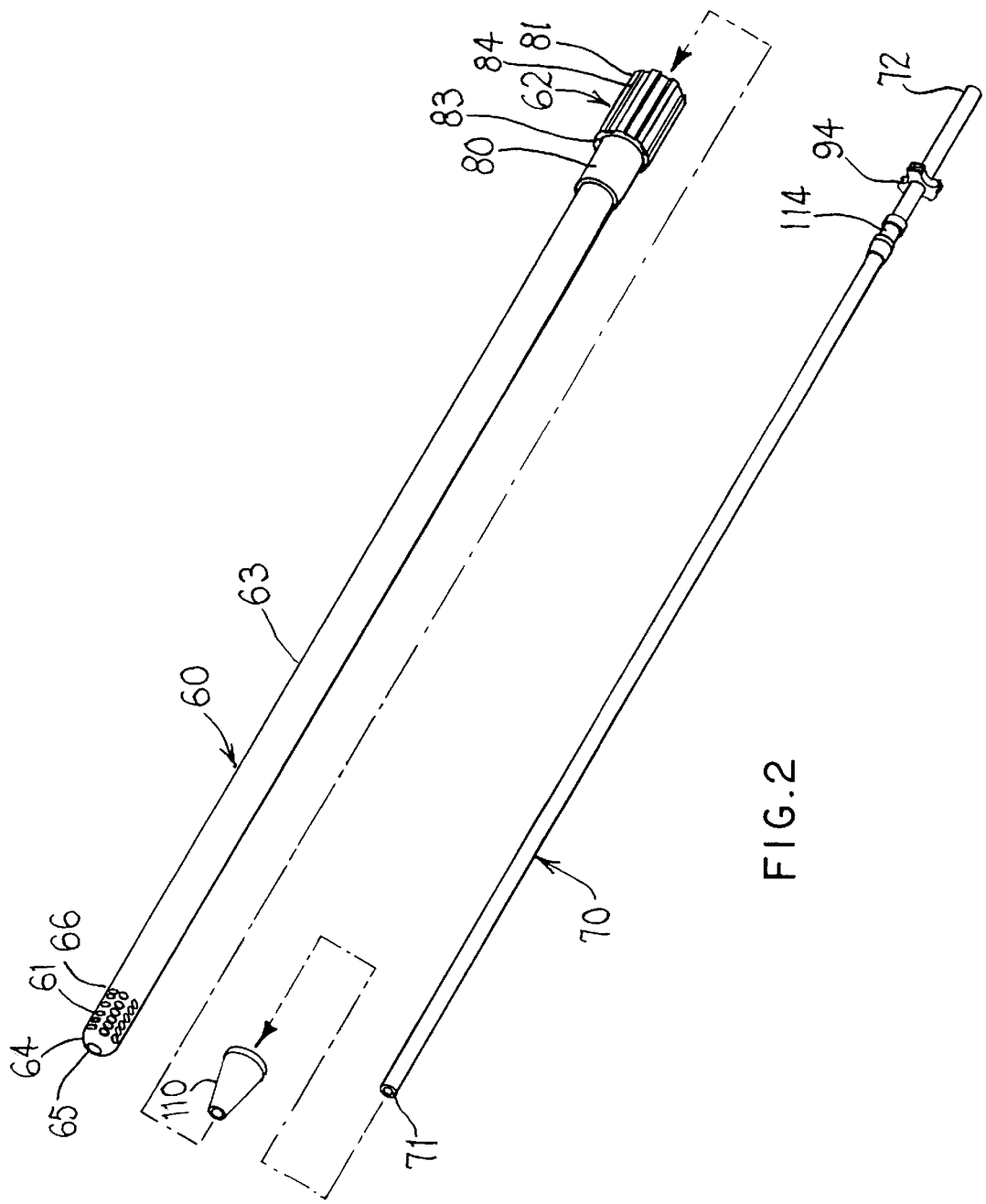
FIG. 2 is an exploded view of a tip according to FIG. 1.

In the preferred embodiment shown, the tip 12 is a suction pool tip for minimizing turbulence near sensitive organs during suction by the suction irrigation apparatus 10. The tip 12 comprises an outer tube 60 having a turbulence minimizing distal end portion 61 (FIG. 2) for insertion in the surgical site SS (FIG. 1) and a proximal end portion, or hub, 62 for connection to the suction irrigation passage 26 of the handpiece 11. The outer tube 60 can be provided in a variety of sizes. For example, units constructed according to the invention have been approximately 5 to 10 millimeters in outside diameter and about 32 centimeters in length, although the invention contemplates outer tubes of lesser or greater diameter and length. The outer tube 60 further comprises a relatively thin walled, rigid metal (preferably stainless steel) tubular sleeve 63 (FIG. 2) whose forward end defines the turbulence minimizing distal end portion 61. The turbulence minimizing distal end portion 61 comprises a convexly rounded end 64 (FIG. 2) having a forward facing central opening 65 for purposes appearing hereinafter. The turbulence minimizing portion of the distal end portion 61 comprises circumferentially and axially spaced suction flow holes 66 opening through the wall of the outer tube 60 into the hollow interior 67 (FIG. 3) thereof. In one unit constructed according to the invention, the holes 66 were provided in 8 axially extending, circumferentially spaced rows, each row including one forward facing hole in the rounded end 64 and 6 holes facing radially outward in the tubular sleeve 63 in the forward portion thereof immediately behind the rounded end 64. Other patterns and numbers of holes are contemplated as well. The suction flow of fluent material rearwardly into the multiplicity of holes 66 minimizes turbulence and risk of damage of sensitive organs during suction.

The tip 12 further includes an inner tube 70 extending lengthwise within the outer tube 60, in a normally fixed but removable manner. The inner tube has an open distal end portion 71 which, in the assembled condition of the apparatus shown in FIGS. 1 and 3, extends forwardly through the central opening 65 in the rounded forward end 64 of the outer tube 60, for providing irrigation liquid to the surgical site.

The inner tube 70 has a proximal end portion 72 (FIGS. 2 and 3) which, in the assembled condition of the apparatus, protrudes rearwardly from the proximal end portion 62 of the outer tube 60 as seen for example in FIGS. 3 and 4, for connection to the suction irrigation passage 26 of the suction irrigation handpiece 11.

Figure 4A:
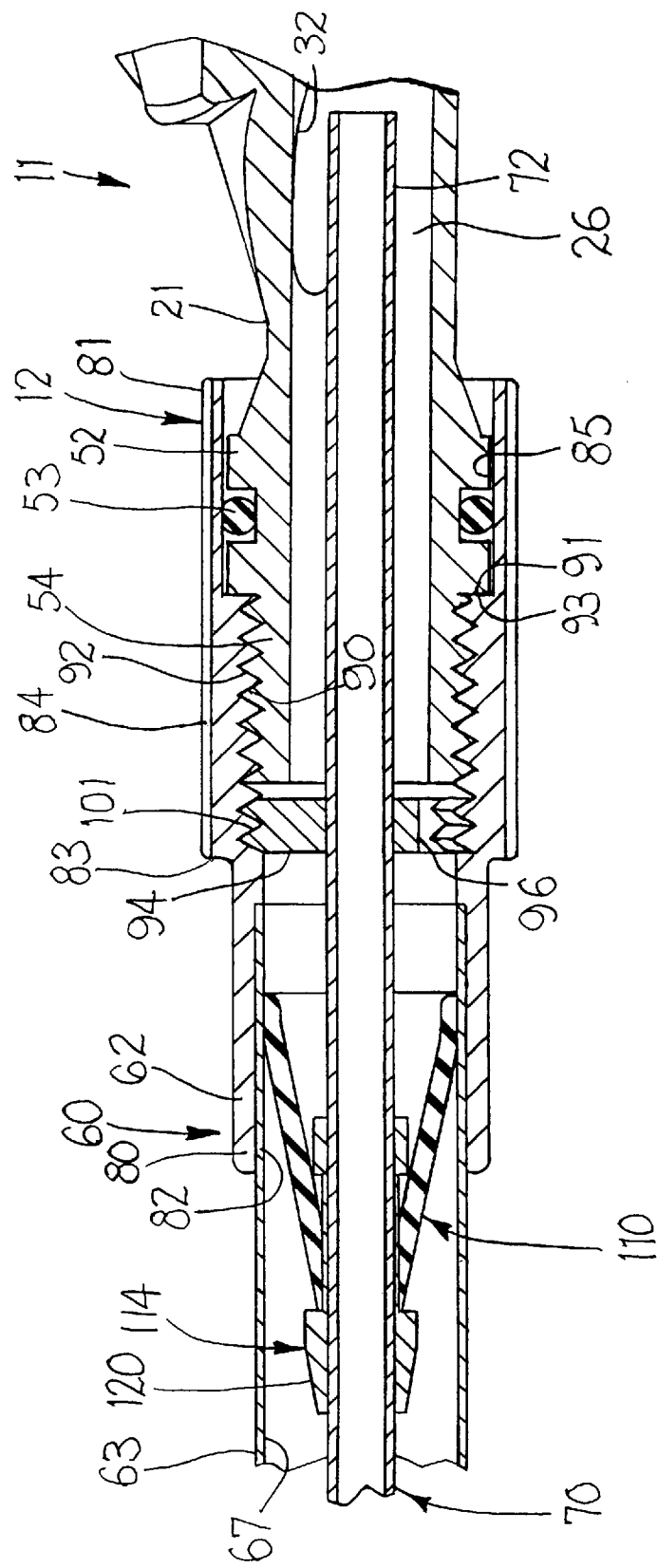
FIG. 4A is an enlarged fragment of FIG. 3 in the region of connection of the tip to the handpiece.

Turning now to the arrangement of the proximal end portions 62 and 72 of the outer and inner tubes 60 and 70 to each other, and to the forward end portion 22 of the handpiece housing conduit 21, attention is directed to FIGS. 1, 4 and 4A. The inner tube is supported at its distal end portion 71(FIG. 1) snugly, but axially slidably, in the distal central opening 65 at the distal end of the outer tube 60.

The proximal end portion, or hub 62 of the outer tube 60 is a hollow, stepped, elongate member having forward and rearward parts 80 and 81 of a generally tubular sleeve-like character. The forward hub part 80 (FIG. 4A) has a radially shallow, axially elongate cylindrical recess 82 formed therein for snugly and fixedly receiving the proximal end portion of the tubular sleeve 63, which is fixed therein by any convenient means such as welding and extends coaxially forwardly therefrom. The forward facing rear end of the recess 82 positively axially locates the rear end of the tubular sleeve 63. Close spaced rearward from forward hub part 80, is integrally located the rearward hub part 81, which steps at 83 radially outward to form a gripping (here axially ribbed) surface 84 for frictional engagement by the hand of the user, to facilitate installation of the tip 12 on handpiece 11. A cylindrical recess 85 (FIG. 4A) opens rearward from the rearward part 81 of the hub 62 and coaxially slidably receives the boss 52 of the handpiece 11, with the O-ring 53 bearing sealingly on the peripheral wall of the recess 85 to prevent axial fluid leakage therebetween. The interior wall of the hub 83 has interior threads 90 (FIG. 4A) extending rearward proximally from exterior step 83 to the rear opening recess 85. The interior threads 90 are spaced radially inboard from the peripheral wall of the rear facing recess 85 by an annular, rear facing step 91. The sleeve-like part 54 of the forward end portion 22 of the conduit 21 of the handpiece 11 is correspondingly externally threaded as indicated at 92 for threading into the internally threaded portion 90 of the hub 62 of the tip 12. When the tip 12 is fully threaded onto the conduit front end portion 22, the annular front end 93 of the conduit boss 52 axially abuts the rear facing step 91 of the tip hub 62 so as to firmly and fixedly, yet releasably, secure the tip 12 on the handpiece 11.

The inner tube 70 has its proximal end portion 72 terminating radially opposite the front port 32 for receiving irrigation liquid therefrom. The inner tube 70 is radially spaced both from the interior 67 of the outer tube 60 and the interior wall of the passage 26 (FIG. 4A) of the handpiece. Accordingly, it is possible for fluid to flow through the inner tube 70 and through the annular space between the inner tube 70 and the outer tube 60 and the peripheral wall of the handpiece central passage 26 between the handpiece and the surgical site SS of FIG. 1.

To maintain substantial coaxiality of the inner tube with respect to the outer tube, and hence with respect to the central passage 26 of the handpiece, a spider-like, multi-perforate collar 94 (FIGS. 2, 4A and 8) is fixed, as by welding, to the outside of the inner tube 70. To this end, the collar 94 includes a central opening 95 (FIG. 8) for receiving the inner tube 70 snugly therethrough. Notches 96 (here 3 in number) are provided in the periphery of the spider collar 94, open radially outwardly therefrom, and occupy a substantial portion of the periphery thereof. The notches 96 are thus separated by remaining, radially outwardly extending leg-like portions (hereafter legs) 100. The periphery of the spider collar 94 (at the radially outer ends of the legs 100) is threaded at 101 for threaded engagement in the internal threads 90 of the tip hub 62, as seen in FIG. 4A. With the spider collar 94 threaded fully forward in the collar 62, to its forwardmost position shown in FIG. 4A, the distal end portion 71 of the inner tube 70 protrudes fully forward from the outer tube 60 as indicated in FIG. 1 and the inner tube is positively fixed within the outer tube in its position of use for surgery. The inner tube 70 is however unthreadable rearward out of the outer tube 60, as for post surgical cleaning and sterilization.

The spider collar 94 and externally threaded sleeve-like part 54 of the handpiece advantageously have the same effective threaded diameter and thread type so that the single internal thread 90 of the tip hub 62 threadedly receives and positively fixes and axially locates, on the outer tube 60, both the inner tube 70 (through its spider collar 94) and the handpiece 11. The threads 90, 92 and 101 are preferably triple lead threads.

A flow responsive one-way seal 110 is interposed between the inner and outer tubes 70 and 60, as indicated in FIGS. 4A and 6. In the preferred embodiment shown, the seal 110 is a flexible, elastomeric, open-ended, frustocone with a hollow narrow end portion 111 for mounting on the inner tube 70 and a flexible wide end 112.

The narrow end portion 111 of the seal 110 includes a coaxial hole 113 (FIG. 7). To facilitate mounting of the seal 110 on the inner tube 70, a tubular adaptor 114 is fixed, as by welding, coaxially on the inner tube 70 at a location spaced forward from the spider collar 94 (here to extend forward from the front end portion of the hub 62 of the outer tube 60, in the assembled condition of the tip 12). The tubular adaptor 114 is substantially spool shaped, having a substantially cylindrical mid-portion 115 (FIG. 7) axially flanked by radially enlarged front and rear heads 116 and 117. The front head has a forwardly tapered nose 120.

Whereas the exterior profile of the seal 110 tapers forwardly (leftwardly in FIGS. 6 and 7), its wall thickness tapers rearwardly as shown in FIG. 7, such that the wide end portion 112 has a lesser wall thickness than the narrow end portion 111. This makes the seal 110 increasingly flexible from its narrow front portion 111 to its wide end portion 112. The rear end of the seal 110 is gently rounded in cross section on the inside as indicated at 122 (FIG. 7) and is cylindrically flattened in cross section at the outside as indicated at 123, which imparts further flexibility at the extreme rear end portion 122, 123 of the seal 110, as well as providing a convex angled break 124 between the cylindrical flat 123 and the frustoconical outer surface 125 of the seal 110 to enhance sealing against the interior surface 67 of the surrounding outer tube sleeve 63.

To assemble the apparatus, the spider collar 94 and tubular adaptor 114 (FIG. 4A) are slid onto and fixed (as by welding) on the inner tube 70 in their positions shown. The frustoconical seal 110 is then slid (wide rear end portion first) rearward over the tapered nose 120 of the tubular adaptor 114, elastically radially outwardly stretching to do so, and then snaps resiliently back radially inward to resiliently and sealingly grip the mid-portion 115 (FIG. 7) in the manner shown in FIG. 4A. The radially enlarged heads 116 and 117 trap the narrow front end portion 111 of the seal 110 axially therebetween, due to their radially enlarged size compared to the mid-portion 115 and also due to their axially opposed, step-like, substantially radial end walls 121. Thus, because of the resilient snug fit of the seal narrow end portion 111 around the mid-portion 115 of tubular adapter 114, and the spool-like radial enlargement of the heads 116 and 117 of the adaptor, the seal 110 is positively trapped on the tubular adaptor 114, despite forward and rearward forces that may be applied to the radially outer portion of the seal during use.

The outer tube 60 is assembled by fixing the hub 62 (as by welding) on the rear end portion of the tubular sleeve 63.

The inner tube 70 can then be inserted forwardly into the outer tube 60. As the distal end portion 71 of the inner tube 70 emerges forwardly through the central opening 65 in the rounded front end 64 of the outer tube (FIG. 3), the inner tube 70 is rotated to thread the spider 94 into the internally threaded portion 90 of the hub 62, until the spider collar 94 bottoms forwardly at the front end of the threaded portion 90. Simultaneously in this forward movement of inner tube into outer tube, the tubular adaptor spool 114 draws the seal 110 into and axially along the hub 62 and into sealing engagement with the interior 67 of the tubular sleeve 63. With assembly completed, the wide rear end portion 112 of the seal 110 is, due to its own resilience and the somewhat smaller diameter of the interior 67 of the tube sleeve 63, is pressed resiliently and sealingly against the interior surface 67 of the tubular sleeve 63 as shown in FIG. 4A.

The rear opening hub 62 of the tip 12 is mounted on the forward end portion 22 of the housing conduit 21 by threading thereonto to its FIG. 4A position, wherein the O-ring 54 seals against leakage of fluid therepast.

In operation, with the irrigation valve IV open, providing irrigation flow as generally indicated in FIG. 4, the flow from the irrigation port 32 is free to enter the inner tube 70 and pass out the distal end portion 71 thereof into the surgical site SS (FIG. 1). However, the wide end portion 112 of the seal 110 (FIGS. 4 and 4A) blocks the tubular sleeve 63 of the outer tube 60, due to the resilient outward pressing of the wide end of the seal 110 against the interior of the tubular sleeve 63. This outward pressing is enhanced by the pressure of the irrigation liquid which passes forwardly through the notches 96 in the spider collar 94 and presses forwardly and radially outwardly against the seal 110 to force its wide end portion 112 even more firmly and sealingly outward radially against the interior of the tubular sleeve 63, thereby creating a positive blockage against the irrigation liquid flow forwardly past the seal 110.

Figure 5:
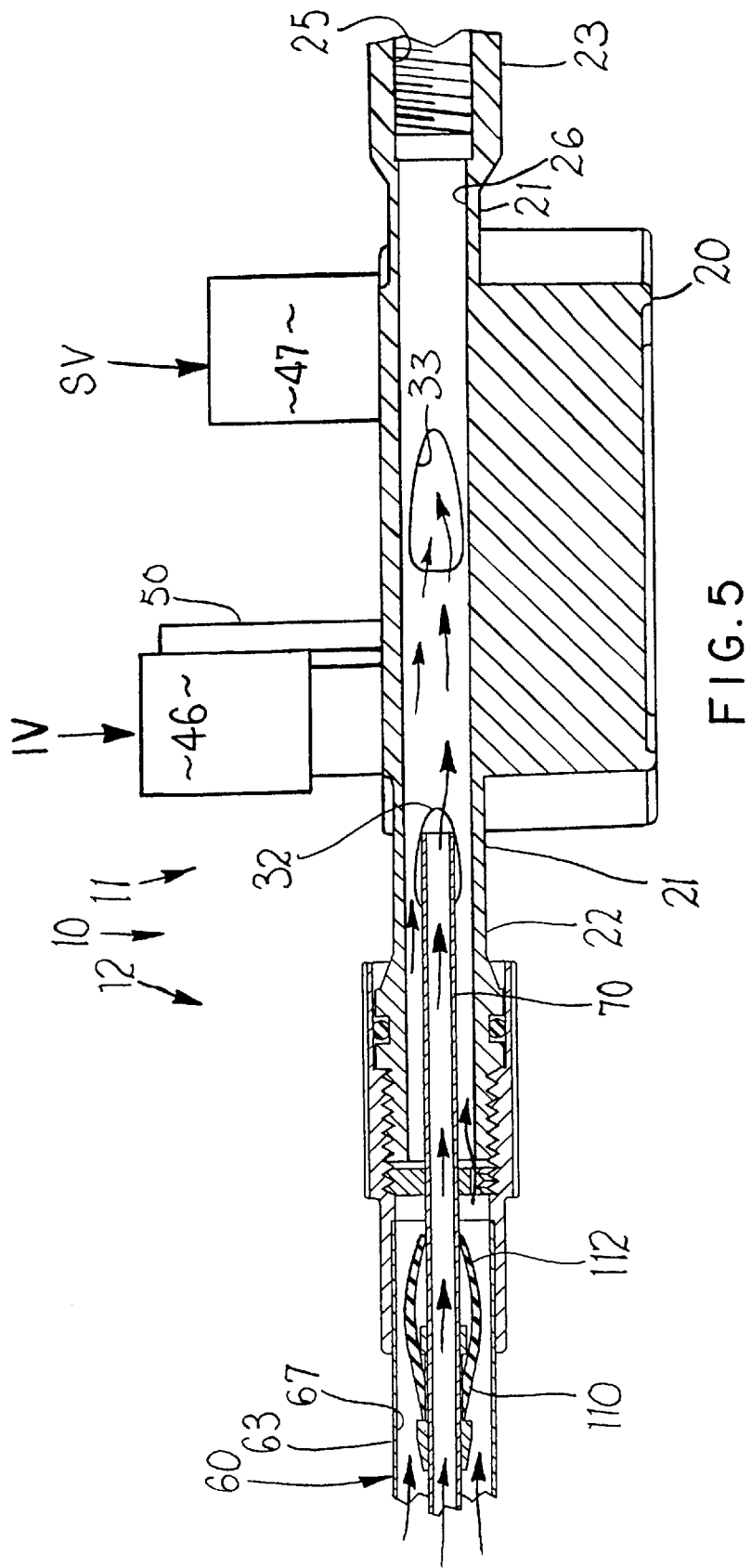
FIG. 5 is a view similar to FIG. 4 but showing the suction flow mode, rather than irrigation flow mode, of the apparatus.

On the other hand, when the irrigation liquid valve IV is closed and the suction valve SV is open, as in FIG. 5, the resulting partial vacuum, or subatmospheric pressure, in the suction port 33 and hence in the handpiece conduit passage 26, is less than the atmospheric pressure at the surgical site SS, thereby creating a pressure drop rearwardly across the seal 110. The rearward pressure drop across the seal 110 distorts the wide end portion 112 thereof, pulling major portions of it away from the interior 67 of the surrounding tubular sleeve 63 of the outer tube 60 and allowing free rearward flow of suctioned fluids and material therepast. Thus, the inventive apparatus permits suction flow, in the direction of the arrows in FIG. 5, through both the inner tube 70 and outer tube 60 into the handpiece central passage 26 and suction port 33.

After use, the tip 12 can be unthreaded from the handpiece. The particular handpiece 11 shown is constructed of inexpensive plastic and can be thrown away after a single use, thereby avoiding the problem of cleaning and sterilizing a multi-part member of relatively complex form. Alternatively, it is contemplated that the tip 12 can be used with a reusable and sterilizable handpiece (not shown).

The tip 12 here shown is preferably constructed of surgical grade stainless steel throughout (except for O-ring 53 and seal 110) and is readily disassembled into relatively simple parts for sterilization and safe further use. More particularly, to disassemble same the steps are essentially opposite those used during assembly, namely the inner tube 70 is threaded rearwardly out of the outer tube 60. It is contemplated that the seal 110 can either be sterilized with the inner tube 70 or discarded and replaced with a freshly sterilized new seal for further use. Separation of the two tubes enhances the ability to safely sterilize same, as by minimizing difficult to sterilize joints, cracks, etc.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical suction tip for minimizing turbulence near sensitive organs during suction by a surgical suction irrigation apparatus, the tip comprising:

an outer tube having a turbulence minimizing distal end portion for communication with a surgical site and means for connecting a proximal end portion thereof to a suction irrigation passage of a suction irrigation handpiece;

an inner tube extending in said outer tube and having an open distal end portion for communication with a surgical site and having means defining an open proximal end portion for connection to a suction irrigation passage of a suction irrigation handpiece;

a flow responsive one way collapsing cone seal interposed between said inner and outer tubes.

2. The tip of claim 1 in which said collapsing cone seal comprises means for:

(1) blocking irrigation flow through said outer tube and channeling irrigation flow through said inner tube in response to irrigation flow from a suction irrigation handpiece to a surgical site, and (2) allowing suction flow through both tubes from a surgical site in response to suction from a suction irrigation handpiece.

3. The tip of claim 1 wherein said collapsing cone seal comprises a central passage extending therethrough and an outer periphery, the entire extent of said outer periphery having a substantially straight and conical cross-sectional profile, said seal further comprising a cylindrical interior forward wall of constant radius defining a first forward portion of said central passage and a conical interior rearwardly diverging wall of continuously increasing radius defining a second rearward portion of said central passage, said conical interior rearwardly diverging wall smoothly adjoining said cylindrical interior forward wall.

4. The tip of claim 1 in which said collapsing cone seal comprises a flexible cone with a narrow end facing toward a distal end of the tip and sealed around said inner tube and a flexible wide end means facing toward a proximal end of said tip for (1) outward flexing into sealing contact with said outer tube in response to irrigation liquid pressure in said proximal end of said tip and (2) collapsing inward away from said outer tube and toward said inner tube during suction flow.

5. The tip of claim 1 in which said collapsing cone seal comprises a flexible elastomeric open ended frustocone with a narrow end resiliently mounted on said inner tube and a wide end alternatively flexible (1) radially outward toward said outer tube and (2) radially inward toward said inner tube in response to (1) irrigation flow and (2) suction flow, respectively.

6. The tip of claim 1 including means for limiting axial sliding of said collapsing cone seal on said inner tube.

7. A surgical suction tip for minimizing turbulence near sensitive organs during suction by a surgical suction irrigation apparatus, the tip comprising:

an outer tube having a turbulence minimizing distal end portion for communication with a surgical site and means for connecting a proximal end portion thereof to a suction irrigation passage of a suction irrigation handpiece;

an inner tube extending in said outer tube and having an open distal end portion for communication with a surgical site and having means defining an open proximal end portion for connection to a suction irritation passage of a suction irrigation handpiece;

a flow responsive one way collapsing cone seal terposed between said inner and outer tubes; and said outer tube distal end portion being convex and multi-perforate and said inner tube opening through said distal end portion of said outer tube.

8. Apparatus comprising a surgical suction tip for minimizing turbulence near sensitive organs during suction and a surgical suction irrigation handpiece engageable with said tip, the apparatus comprising:

a tip including:
(a) an outer tube having a turbulence minimizing distal end portion for connection with a surgical site and means for connecting a proximal end portion thereof to a suction irrigation passage of a suction irrigation handpiece,
(b) an inner tube extending in said outer tube and having an open distal end portion for communication with a surgical site and having means defining an open proximal end portion for connection to said suction irrigation passage of said suction irrigation handpiece, and
(c) a hub defining the proximal end portion of said outer tube, said hub having a single internal thread for connection to both said suction irrigation handpiece and said inner tube;

a handpiece including a hollow conduit, means for supplying suction and irrigation liquid to said hollow conduit, said conduit having an external thread for engaging said internal thread of said tip hub and positively fixing said tip on said handpiece, said conduit defining the suction irrigation passage of said handpiece, said inner tube having fixed thereon an axially multi-perforate collar, said collar having an external thread engaged with said single internal thread of said hub distally of said suction irrigation handpiece, said conduit having the same effective diameter as said collar and lying closely adjacent same in said hub, such that both said handpiece conduit and collar are threaded in the same thread of said tip hub.

9. A surgical suction tool for minimizing turbulence near sensitive organs during suction by a surgical suction irrigation apparatus of a kind having a suction irrigation handpiece with a hollow conduit having an external thread and defining a suction irrigation passage, the tip comprising:

an outer tube having a turbulence minimizing distal end portion for connection with a surgical site and means for connecting a proximal end portion thereof to a suction irrigation passage of a suction irrigation handpiece;
an inner tube extending in said outer tube and having an open distal end portion for communication with a surgical site and having means defining an open proximal end portion for connection to a suction irrigation passage of a suction irrigation handpiece and having an externally threaded portion;
a hub defining the proximal end portion of said outer tube, said hub having a single means for connection to both (1) a suction irrigation handpiece and (2) said inner tube, said single means being a single internal thread engaging said externally threaded portion, and said single internal thread extending axially beyond said externally threaded portion for positively fixing said tip to a handpiece.

10. The tool of claim 9 including a suction irrigation handpiece having means for supplying suction and irrigation liquid at a hollow conduit, said conduit having an external thread for engaging said internal thread of said tip hub and positively fixing said tip on said handpiece, said conduit defining the suction irrigation passage of said handpiece.

11. The apparatus of claim 10 in which said inner tube externally threaded portion comprises an axially multi-perforate collar externally threaded to threadedly engage said single internal thread of said hub distally of said suction irrigation handpiece, said conduit having the same effective diameter as said collar and lying closely adjacent same in said hub, such that both said handpiece conduit and collar are threaded in the same thread of said tip hub.

12. A surgical suction tip for minimizing turbulence near sensitive organs during suction by a surgical suction irrigation apparatus, the tip comprising:

an outer tube having a turbulence minimizing distal end portion for communication with a surgical site and means for connecting a proximal end portion thereof to a suction irrigation passage of a suction irrigation handpiece;
an inner tube extending in said outer tube and having an open distal end portion for communication with a surgical site and having means defining an open proximal end portion for connection to a suction irrigation passage of a suction irrigation handpiece;
a flow responsive one way seal with an unobstructed flow path between said inner and outer tubes; and
a one-piece tubular mounting member for mounting said seal on said inner tube, said mounting member being disposed about said inner tube between said inner tube and said seal, said mounting member being generally spool-shaped and having a radially enlarged forwardly tapering nose at a front end portion thereof, a radially enlarged head at a rear end portion thereof, and a radially recessed intermediate portion disposed between said nose and said head, a portion of said seal being snap-fitted within said recessed intermediate portion to limit axial sliding of said seal on said inner tube.

13. The tip of claim 12 in which said seal comprises means for:
(1) blocking irrigation flow through said outer tube and channeling irrigation flow through said inner tube in response to irrigation flow from a suction irrigation handpiece to a surgical site, and
(2) allowing suction flow through both tubes from a surgical site in response to suction from a suction irrigation handpiece.

14. The tip of claim 12 wherein said seal comprises a cone seal, said snap-fitted portion of said seal comprising a radially narrow end of said seal, said seal further comprising a radially wide end extending axially beyond said radially enlarged head at said rear end portion of said mounting member.

15. A surgical suction tip for minimizing turbulence near sensitive organs during suction by a surgical suction irrigation apparatus, the tip comprising:

an outer tube having a turbulence minimizing distal end portion for communication with a surgical site and means for connecting a proximal end Portion thereof to a suction irrigation passage of a suction irrigation handpiece;
an inner tube extending in said outer tube and having an open distal end portion for communication with a surgical site and having means defining an open proximal end portion for connection to a suction irrigation passage of a suction irrigation handpiece;
a flow responsive one way seal with an unobstructed flow path between said inner and outer tubes; and
said outer tube distal end portion being convex and multi-perforate and said inner tube opening through said distal end portion of said outer tube.

* * * * *

UNITED STATES PATENT AND TRADEMARK OFFICE
CERTIFICATE OF CORRECTION

PATENT NO. : 5,827,218
DATED : October 27, 1998
INVENTOR(S) : John NGUYEN et al

It is certified that error appears in the above-identified patent and that said Letters Patent is hereby corrected as shown below:

Column 8, line 63;  change "terposed" to ---interposed---.

Column 10, line 52; change "Portion" to ---portion---.

Signed and Sealed this

Second Day of November, 1999

*Attest:*

Q. TODD DICKINSON

*Attesting Officer*    Acting Commissioner of Patents and Trademarks